Figure 1:
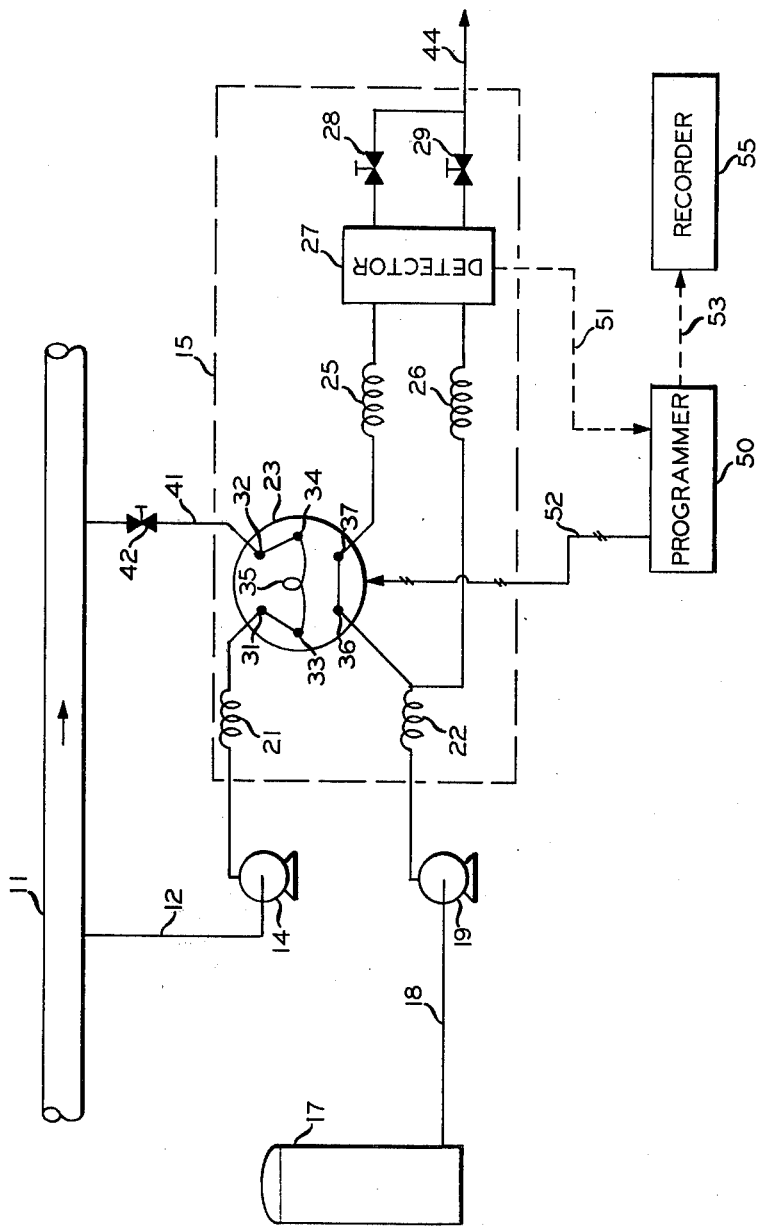

United States Patent [19]

Porter

[11] 4,016,074
[45] Apr. 5, 1977

[54] CHROMATOGRAPHIC SEPARATION
[75] Inventor: Grady T. Porter, Bartlesville, Okla.
[73] Assignee: Phillips Petroleum Company, Bartlesville, Okla.
[22] Filed: Aug. 5, 1975
[21] Appl. No.: 602,179
[52] U.S. Cl. .......................... 210/31 C; 210/198 C
[51] Int. Cl.² ........................................ B01D 15/08
[58] Field of Search .......... 210/31 C, 24 C, 198 C; 55/67, 197

[56] References Cited
UNITED STATES PATENTS

| | | | |
|---|---|---|---|
| 2,287,732 | 6/1942 | Frey | 423/528 |
| 2,430,673 | 11/1947 | Gibson et al. | 260/671 |
| 3,246,047 | 4/1966 | Chapman et al. | 260/683.48 |
| 3,352,643 | 11/1967 | Ando et al. | 23/230 |
| 3,522,725 | 8/1970 | Waters | 210/31 C |
| 3,846,297 | 11/1974 | Thaw | 210/24 C |

OTHER PUBLICATIONS

Introduction to Modern Liquid Chromatography by Snyder and Kirkland, John Wiley and Sons, New York, N. Y., Rec. Scientific Library June 23, 1974, pp. 218, 219, 269–271 relied on.

A Rapid Method of Identification and Assessment of Total Crude Oils and Crude Oil Fractions by Gel Permeation Chromatography by J. N. Done and W. K. Reid, Presented before the Div. of Pet. Chem., ACS at Houston, Tex., Feb. 1970.

Primary Examiner—John Adee

[57] ABSTRACT

In the liquid chromatographic analysis of a sample containing two or more constituents which are chromatograhically separable using an aqueous ether carrier liquid, an effective amount of water is added to the chromatographic carrier liquid thereby increasing the efficiency of the chromatographic separation and decreasing the incidence of chromatographic column plugging. In a preferred embodiment, addition of a small amount of water to a tetrahydrofuran carrier liquid results in substantial improvement in the analysis of a sulfuric acid alkylation catalyst wherein a sample containing sulfuric acid and other chromatographically separatable organic materials is separated in order to measure the relative proportions of sulfuric acid and hydrocarbon or other materials within the sample.

24 Claims, 2 Drawing Figures

CHROMATOGRAPHIC SEPARATION

This invention relates to chromatographic separation. In another aspect the invention relates the chromatographic separation associated with liquid chromatographic analysis. In yet another aspect the invention relates to chromatographic analysis of liquid samples. In another aspect the invention relates to chromatographic separation of sulfuric acid from organic materials, particularly hydrocarbon materials. In still another aspect the invention relates to chromatographic separation of sulfuric acid from other constituents found in a sulfuric acid alkylation catalyst. In another aspect the invention relates to an improved carrier liquid for use in the chromatographic separation of acid and hydrocarbon or other organic sample constituents.

The development of liquid chromatographic analysis equipment and methods suitable for field and plant use under commercial plant conditions has been accompanied by the need for chromatographic separation techniques which lend themselves readily to use in the analysis of process liquids which contain various unknown impurities, or which otherwise present varying degrees of unexpected difficulty in performing an analysis. For example, the use of commercial grade materials as well as the conditions and other materials encountered by process liquids can result in difficulties in analyzing a liquid taken from a commercial process. For commercial plant use, particularly for control of the process streams and conditions, the analysis time must be relatively short and the analysis must provide reliable data.

In the process of sulfuric acid alkylation of petroleum feedstocks, for instance, the sulfuric acid catalyst is, over a period of time, diluted by acid soluble oils and other substances which may come in contact with the acid catalyst in the alkylation process. Attempts to analyze such a used commercial catalyst by practical, continuing process liquid chromatographic analysis were initially unsuccessful since the chromatographic column length and pressures required to achieve the desired separation were higher than those suitable for desired low maintenance equipment operation and would not permit the chromatographic separation to be made in a reasonably short period of time. In addition, continued cyclic operation of the chromatographic separation apparatus would result in plugging of the chromatographic column in a very short period of time thereby making continuing analysis of a process impractical and, in economic terms, impossible.

Accordingly, an object of the invention is to provide improved chromatographic separation. Another object is to provide improved chromatographic separation associated with liquid chromatographic analysis. Yet another object of the invention is to provide chromatographic separation of sulfuric acid for organic materials, particularly hydrocarbon materials. Still another object of the invention is to provide chromatographic separation of sulfuric acid from other constituents of a sulfuric acid alkylation catalyst. Another object of the invention is to provide an improved carrier liquid for use in said chromatographic separation of acid and hydrocarbon sample constituents. Yet another object of the invention is to provide improved chromatographic analysis of liquid samples.

In accordance with the invention, an effective amount of water is added to a suitable liquid chromatographic carrier solvent to provide a chromatographic carrier liquid. Flow of the carrier liquid is established through a chromatographic separation column. The sample to be analyzed is injected into the carrier liquid stream upstream of the chromatographic separation column and is carried into the separation column by the carrier liquid. Compared with liquid chromatographic analysis not utilizing a carrier liquid containing water, use of the invention to separate sulfuric acid and hydrocarbon constituents of a sulfuric acid alkylation catalyst can be accomplished utilizing a shorter chromatographic column with less pressure drop across the column and without column plugging. It is particularly surprising that alteration of the carrier solvent by the addition of water both increases the effectiveness of the separation within the chromatographic column and prevents plugging of the column.

Figure 2:
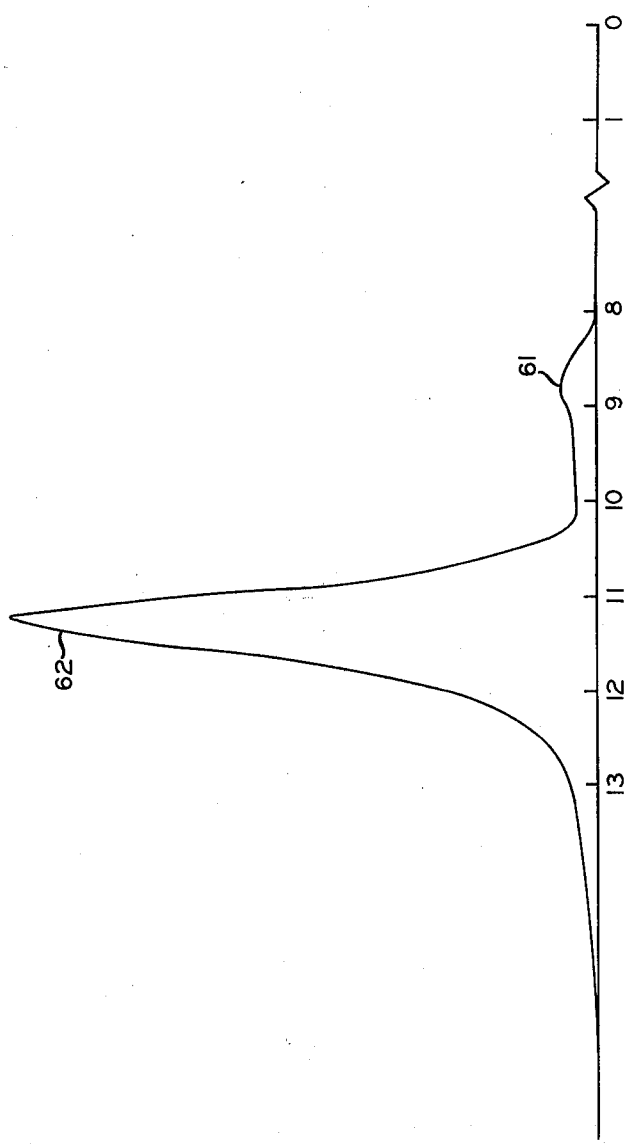

Additional objects and advantages of the invention will be apparent to those skilled in the art from a study of the specification of the invention and the appended claims thereto, and from the drawing in which:

FIG. 1 is a schematic representation of a chromatographic analysis system operated in accordance with the invention, and FIG. 2 is a chromatogram obtained from operation of a chromatographic system in accordance with the invention.

Referring to FIG. 1 in detail, there is illustrated a process conduit 11 carrying a liquid process stream to be analyzed. A portion of the liquid material is withdrawn from the conduit 11 through a conduit means 12 containing a pump means 14 and is delivered to a liquid chromatographic analyzer 15. Where suitable pressure or pressure differential to establish the required sample material flow is provided by the liquid stream within the process conduit 11, the pump means 14 can be omitted from the conduit 12.

In a similar manner a carrier liquid is withdrawn from a carrier liquid supply means 17 through a conduit means 18 which includes a suitable pump means 19 and is delivered to the liquid chromatographic analyzer 15.

Within a temperature controlled portion of the analyzer 15 are a sample heat exchange means 21, a carrier liquid heat exchange means 22, a sample valve means 23, a chromatographic separation column 25, a reference pressure equalization means 26, a chromatographic detector 27, a downstream analysis flow restriction means 28, and a downstream reference flow restriction means 29. The sample valve means 23 is equipped with a sample inlet port 31, a sample outlet port 32, a pair of sample loop ports 33 and 34 having a sample loop 35 operably connected therebetween, a carrier inlet port 36, and a carrier outlet port 37. The sample valve means 23 has two operating positions. In the first position, illustrated by FIG. 1, the sample inlet port 31 is in communication with the sample loop port 33, the sample outlet port 32 is in communication with the sample loop port 34, and the carrier inlet port 36 in in communication with the carrier outlet port 37. In the second position (not illustrated) the sample inlet port 31 is in communication with the sample outlet port 32, the carrier inlet port 36 is in communication with the sample loop port 33, and the carrier outlet port 37 is in communication with the sample loop port 34.

As the sample material in the conduit means 12 is delivered by the pump means 14, or any other suitable source of fluid pressure, to the chromatographic analyzer 15, the sample material enters the heat exchange means 21 which can be any suitable means, such as a preselected length of tubing, which will permit the sample material to reach a desired equilibrium temperature condition inside the chromatographic analyzer 15 prior to delivery of the sample material to the sample valve means 23. When the sample valve means is in the first position illustrated by FIG. 1, sample material enters the sample valve through the sample inlet port 31, flows through the sample loop 35, and exits the sample valve means 23 through the sample outlet port 32. A suitable conduit means 41 carries the sample material leaving the analyzer 15 through the sample outlet port 32 for disposition as appropriate. The sample material can be returned to the process stream from which it came, as illustrated, or can be suitably discarded or disposed of in any manner known to the art and appropriate for the particular material or materials contained within the sample liquid. While use of a flow restriction means 42, such as the illustrated valve, is preferred in order to assure that sufficient pressure is maintained within the sample loop 35 to avoid any sample vaporization within the sample loop, the flow restriction means 42 may not be necessary in many cases where the temperature and pressure within the sample loop 35 and/or the nature of the sample material are such that a positive source of back pressure is not required. In addition to a flow restriction means 42, such as the valve illustrated, a length of small diameter or restricted tubing or any other suitable similar flow restriction means may be utilized. With the sample valve means 23 in the position illustrated, therefore, a continuing supply of sample material from the process stream within the process conduit 11 is provided to and carried through the sample loop 35 so that an up-to-date sample is always ready within the sample loop 35 for injection into the liquid carrier stream flowing to the chromatographic separation column 25.

The carrier liquid entering the chromatographic analyzer 15 from the conduit means 18 and associated pump means 19 is brought to the desired thermal equilibrium conditions within the analyzer 15 as it flows through the heat exchange means 22 which, like the heat exchange means 21 associated with the sample stream, can be any suitable means for bringing the liquid therein to the desired equilibrium temperature under the particular temperature and flow conditions to be encountered. At the outlet of the heat exchange means 22, a portion of the carrier liquid stream is provided to the inlet of the reference pressure equilization means 26. The remainder of the carrier liquid exiting the heat exchange means 22 is provided to the carrier inlet port 36 of the sample valve 23. With the sample valve 23 in its first position, as illustrated, the carrier liquid flows directly to the carrier outlet port 37 and into the chromatographic separation column 25. The chromatographic separation column 25 can be any suitable column of appropriate size and length and containing a chromatographic medium suitable for separating two or more constituents of the sample material obtained from the conduit 11. The reference pressure equilization means 26 can be a column identical, or similar to, the chromatographic separation column 25 or can be any other suitable means such as a valve, capillary tube, restricted tubing length, or other similar means for providing a flow resistance substantially equal to the combined flow resistance of the chromatographic separation column 25 and the sample valve means 23 under the analysis flow conditions which will be encountered.

The detector means 27 will therefore accept a stream of material from the outlet of the chromatographic separation column 25 and a stream of material of substantially equal pressure from the outlet of the reference pressure equalization means 26. Although any suitable detector means 27 can be utilized, a preferred detector means 27 is one which utilizes a differential measurement, comparing a property of the stream delivered thereto by the chromatographic separation column 25 with the same property of the reference stream delivered thereto by the reference flow restriction means 26. One such preferred device is a differential refractometer in which the refractive index of each of the two streams delivered to the detector is utilized to produce a detector output signal 51.

Flow restriction means 28 and 29 downstream of the detector means 27 are utilized to provide sufficient back pressure for the streams flowing through the detector means 27 from the chromatographic separation column 25 and the reference flow restriction means 26 to prevent vaporization of material within the detector means 27 or within any other portion of the upstream analyzer apparatus. The flow restriction means 28 and 29 can be any suitable means for performing the required function including valves, capillary tubes, conduit restrictions, or other similar means. Liquid materials exiting the flow restriction means 28 and 29 can be delivered to a disposal conduit 44 which can carry the materials to a suitable location at which they can be appropriately disposed of.

A programmer means 50 can be provided for timing and controlling the operation of the analyzer 15 and for conditioning the output signal 51 from the detector means 27. Among the various functions performed by the programmer 50 can be the application of a suitable signal 52 to actuate the sample valve means 23 and inject the sample contained in the sample loop 35 into the carrier liquid stream flowing to the chromatographic separation column 25. In addition, the programmer can provide a chromatographic output signal 53, obtained by appropriate conditioning of the detector output signal 51, to a recording means 55 or to a computer means or other similar process control means.

At an appropriate time, as determined by the programmer means 50, a signal 52 is applied by the programmer 50 to the sample valve means 23 thereby placing the sample valve means 23 in its second position. In this position, the sample material within the sample loop 35 is forced by carrier liquid entering the sample valve means 23 through the carrier inlet port 35 through the sample loop 35 and out the carrier outlet port 37 into the chromatographic separation column 25. After sufficient time has elapsed for the sample material within the sample loop 35 to have been removed from the valve means through the carrier outlet port 37, the sample valve means 23 can be returned to its first position in preparation for initiation of a subsequent sampling step. As the various constituents of the sample material are eluted through the chromatographic separation column 25, their presence is sensed by the detector means 27 as, for example, a difference in refractive index between the reference carrier liquid entering detector means from the reference flow restriction means 26 and the liquid entering the detector means from the chromatographic separation column 25.

In an analysis of the sample material containing an acid and acid soluble organic material, particularly one or more hydrocarbon materials, the carrier liquid material ordinarily chosen is any suitable liquid material in which the particular acid and organic material encountered are partially soluble and which possesses the stability, viscosity, and other similar physical characteristics required to properly carry a sample to be analyzed to the chromatographic separation column. In the analysis of a sample comprising sulfuric acid containing hydrocarbon materials dissolved therein, use of a suitable ether such as tetrahydrofuran as a major constituent of the carrier liquid is preferred. Other suitable ethers such as dioxane or 1,2-dimethoxyethane can also be expected to perform satisfactorily under many of the various operating conditions and in conjunction with various sample composition ranges and column packing materials which can be encountered in the practice of the invention.

In accordance with the invention, the amount of water to be incorporated into the carrier liquid must be soluble in an amount at least equal to the concentration to be used therein so that separation of the carrier liquid constituents under chromatographic separation and detection conditions is not encountered. The amount of water which is incorporated into the suitable solvent material can be any amount which is effective for the purpose of improving chromatographic separation within the chromatographic separation column, reducing plugging of the chromatographic column, or both increasing the efficiency of sample constituent separation and reducing column plugging. Under appropriate circumstances water concentrations of as much as 10% or more by volume are considered to be within the scope of the invention. When the volume of the sample material injected by the sample loop 35 is small compared to the flow rate of carrier liquid to the sample valve 23 and chromatographic separation column 25, a very small amount of water in the carrier liquid is sufficient. Under most circumstances less than about 5 percent by volume of water based on the total volume of carrier liquid is desirable. Water concentrations within the range of from about 1 percent by volume to about 5 percent by volume are preferred. The use of water as a carrier liquid constituent surprisingly eliminates chromatographic column plugging as well as improving the efficiency of the chromatographic separation within the chromatographic column.

Any suitable packing materials for use with a chromatographic separation column employing a liquid carrier and capable of performing the desired separation between acid and acid soluble materials can be utilized as the column packing within the chromatographic separation column 25. Preferred packing materials for use in making such separations when a liquid carrier comprising a mixture of an ether and water, particularly tetrahydrofuran and water, is utilized are various commercially available silica materials such as silica gels specially prepared for use as liquid chromatographic column packing materials. The preferred packing materials include silica gels available in particle sizes ranging from about 15 to about 50 microns.

The invention is particularly well suited for the analysis of a sulfuric acid catalyst used in a sulfuric acid alkylation process. Such a catalyst will ordinarily contain a major proportion, usually in excess of about 75 percent, of sulfuric acid with the remainder of the catalyst material being acid soluble oils as well as other various organic or inorganic materials which become dissolved in or otherwise associated with the sulfuric acid catalyst during the course of the alkylation process. The ability to analyze the sulfuric acid content of such a catalyst is advantageous in that it permits either manual or automatic initiation or control of catalyst purification procedures based on the relative amounts of sulfuric acid and additional constituents within the catalyst material. The following examples are illustrative of the advantages of the invention which make continuing routine analysis of such catalyst materials possible.

EXAMPLE I

Liquid chromatographic analysis of an actual sample of sulfuric acid alkylation catalyst was attempted utilizing the apparatus schematically illustrated by FIG. 1 wherein the liquid chromatographic analyzer 15 and programmer 50 were a Model 102 process chromatograph and programmer manufactured by Applied Automation, Inc., Bartlesville, Oklahoma. The sample valve means 23 employed was a Model 8 high pressure sample valve manufactured by Seiscore, Tulsa, Oklahoma. The sample valve contained an internal 2 microliter sample loop. The chromatographic separation column 25 used was a ⅛ inch diameter stainless steel column approximately 8 ft. in length and packed with a commercially available silica having an average pore diameter of about 150 angstroms, a surface area of about 300 sq. meters per gram, and a particle size in the range of from about 15 to 25 microns. (Porasil T, available from Waters Associates, Framingham, Mass.). Tetrahydrofuran was utilized as the liquid carrier material. In order to obtain a flow rate of carrier material through the chromatographic column of approximately 1 milliliter per minute, the pressure necessary to force the liquid through the column was approximately 1300 pounds per square inch. Under these conditions the elution time through the column was aproximately 30 minutes. Although a shorter chromatographic column would have made it possible to obtain the same flow rate utilizing less column pressure, the approximately 8 ft. of column used was necessary in order to obtain adequate sulfuric acid and hydrocarbon peak resolution. Although separation of the sulfuric acid and hydrocarbon constituents of the catalyst was accomplished, both the 30-minute elution time and high pressure required were undesirable for either unattended operation or responsive process control. In addition, due to apparent impurities in the sample which were not dissolved by the tetrahydrofuran, loss of accuracy and peak resolution was observed after only a few analysis cycles, and within one day of operation the chromatographic separation column was plugged.

EXAMPLE II

Using the same chromatagraphic analyzer and programmer and the same sample valve, while substituting a carrier liquid of 97 percent by volume tetrahydrofuran and 3 percent by volume water and substituting a 4 ft. chromatrographic column of the same diameter and packed with the same commercially available silica material as the longer column of Example I, a flow rate of approximately one milliliter per minute of carrier liquid through the chromatographic separation column was achieved with a pressure drop across the separation column of approximately 600 pounds per sq. inch. Two distinct advantages were observed in the analysis of the sulfuric acid alkylation catalyst using the tetrahydrofuran/water mixture as a carrier. Adequate chromatographic peak resolution of the hydrocarbon material peak and the sulfuric acid peak (peaks 61 and 62, respectively of FIG. 2) was obtained even though the separation column used was only half the length of the column of Example I, and the elution time required was reduced to less than 15 minutes. In addition, after 3 months of continuous cyclic operation, the chromatographic separation column showed no signs of column plugging.

Although the invention has been described and illustrated herein in conjunction with a preferred embodiment thereof, adaptation of the invention for use in analyzing other liquids containing acids and organic materials, use of various suitable column packing materials, use of various suitable carrier solvent materials, and other reasonable variations and modifications within the capability of those skilled in the art are considered to be within the scope of the invention.

I claim:

1. A process comprising:
   establishing a flow of carrier liquid, comprising a suitable ether solvent and an effective amount of water for preventing column plugging, through a packed chromatographic column suitable for separating hydrocarbon materials from an acid;
   introducing a liquid sample material comprising an acid and hydrocarbon material into said carrier liquid upstream of said chromatographic column; and
   passing said carrier liquid containing said sample material through said chromatographic column to separate said acid from said hydrocarbon material.

2. A process in accordance with claim 1 wherein said acid comprises sulfuric acid and said solvent material comprises an ether suitable as a liquid chromatographic carrier for both sulfuric acid and hydrocarbons.

3. A process in accordance with claim 2 wherein said carrier liquid contains up to about 5% by volume, based on the total carrier liquid volume, of water.

4. A process in accordance with claim 3 wherein said ether comprises tetrahydrofuran.

5. A process in accordance with claim 4 wherein said sample liquid material comprises at least about 75% by volume, based on the total sample material volume, of sulfuric acid.

6. A process in accordance with claim 4 wherein said sample liquid material comprises sulfuric acid catalyst material from a sulfuric acid alkylation process.

7. A process in accordance with claim 6 wherein passing said carrier liquid containing said sample material through said chromatographic column comprises contacting said carrier liquid and sample material with a silica column packing.

8. A process in accordance with claim 7 wherein said column packing comprises silica having an average pore size of about 150 angstroms and a surface area of about 300 square meters per gram.

9. A process in accordance with claim 8 wherein said silica has a particle size within the range of from about 15 to about 25 microns.

10. A process in accordance with claim 9 wherein said sample liquid material comprises at least about 75% by volume, based on the total sample material volume, of sulfuric acid.

11. A process in accordance with claim 10 wherein said carrier liquid consists essentially of about 97% by volume of tetrahydrofuran and about 3% by volume of water.

12. A process in accordance with claim 1 wherein said sample liquid material comprises at least about 75% by volume, based on the total sample material volume, of sulfuric acid.

13. A process in accordance with claim 12 wherein said solvent material comprises an ether suitable as a liquid chromatographic carrier for both sulfuric acid and hydrocarbons.

14. A process in accordance with claim 13 wherein passing said carrier liquid containing said sample material through said chromatographic column comprises contacting said carrier liquid and sample material with a silica gel column packing.

15. A process in accordance with claim 14 wherein said carrier liquid contains up to about 5% by volume, based on the total carrier liquid volume, of water.

16. A process in accordance with claim 14 wherein said sample liquid material comprises sulfuric acid catalyst material from a sulfuric acid alkylation process.

17. A process comprising:
   establishing a flow of carrier liquid, comprising a suitable ether and an amount of water effective to prevent column plugging, through a packed chromatographic column packed with a solid chromatographic separation material suitable for separating hydrocarbon materials from an acid;
   introducing a liquid sample material comprising an acid and hydrocarbon material into said carrier liquid upstream of said chromatographic column; and
   passing said carrier liquid containing said sample material through said chromatographic column to separate said acid from said hydrocarbon material.

18. A process in accordance with claim 17 wherein establishing said flow of carrier liquid through said packed chromatographic column comprises establishing said flow through a column packed with a silica material.

19. A process in accordance with claim 18 wherein said carrier liquid contains up to about 5% by volume, based on the total carrier liquid volume, of water.

20. A process in accordance with claim 19 wherein said chromatographic separation column is packed with a silica gel packing material.

21. A process in accordance with claim 20 wherein said column packing comprises silica having an average pore size of about 150 angstroms and a surface area of about 300 square meters per gram.

22. A process in accordance with claim 21 wherein said silica has a particle size within the range of from about 15 to about 25 microns.

23. A process in accordance with claim 22 wherein said ether comprises tetrahydrofuran.

24. A process in accordance with claim 23 wherein said sample liquid material comprises sulfuric acid catalyst material from a fulfuric acid alkylation process.

* * * * *